United States Patent
Stenton (10) Patent No.: US 7,094,250 B2
(45) Date of Patent: Aug. 22, 2006

(54) MULTIPLE FUNCTION MEDICAL ADHESIVE APPLICATOR

(75) Inventor: Richard J. Stenton, Horrabridge (GB)

(73) Assignee: MedLogic Global Limited, Cheshire (GB)

(*) Notice: Subject to any disclaimer, the term of this patent is extended or adjusted under 35 U.S.C. 154(b) by 488 days.

(21) Appl. No.: 10/209,317

(22) Filed: Jul. 30, 2002

(65) Prior Publication Data
US 2003/0032980 A1 Feb. 13, 2003

Related U.S. Application Data

(60) Provisional application No. 60/308,866, filed on Aug. 1, 2001.

(51) Int. Cl.
*A61B 17/08* (2006.01)

(52) U.S. Cl. .................. 606/213; 222/546

(58) Field of Classification Search .......... 401/40, 401/118, 126, 129, 130; 414/904; D19/66, D19/70, 71; 606/92–94, 213–215
See application file for complete search history.

(56) References Cited

U.S. PATENT DOCUMENTS

| | | | |
|---|---|---|---|
| 4,053,243 A * | 10/1977 | Levin | 401/186 |
| 5,480,935 A | 1/1996 | Greff et al. | |
| 5,962,010 A * | 10/1999 | Greff et al. | 424/443 |
| 6,099,807 A | 8/2000 | Leung | |
| 6,224,799 B1 | 5/2001 | Gould | |
| 6,283,933 B1 | 9/2001 | D'Alessio et al. | |
| 6,322,852 B1 | 11/2001 | Leung | |
| 6,340,097 B1 | 1/2002 | D'Alessio et al. | |
| 6,372,713 B1 | 4/2002 | Redei | |
| 6,425,704 B1 * | 7/2002 | Voiers et al. | 401/196 |
| 6,428,233 B1 | 8/2002 | Clark et al. | |
| 6,428,342 B1 | 8/2002 | Pan | |

FOREIGN PATENT DOCUMENTS

| | | |
|---|---|---|
| EP | 0 390 922 A1 | 10/1990 |
| WO | WO 93/25196 A1 | 12/1993 |
| WO | WO 99/30629 A | 6/1999 |
| WO | WO 01/51218 A1 | 7/2001 |

* cited by examiner

*Primary Examiner*—Glenn K. Dawson
(74) *Attorney, Agent, or Firm*—Foley & Lardner LLP

(57) ABSTRACT

An adhesive applicator for applying medical adhesives, and particularly cyanoacrylates is disclosed. The applicator includes a body forming an internal reservoir and an opening between the internal reservoir and the exterior of the body, a sponge disposed over the opening, a slotted tip nozzle disposed over the sponge, and a small orifice tip nozzle disposed over the slotted tip nozzle.

12 Claims, 4 Drawing Sheets

FIG 8

MULTIPLE FUNCTION MEDICAL ADHESIVE APPLICATOR

PRIORITY CLAIM

This application claims priority under 35 U.S.C.§ 119 to U.S. Provisional Application No. 60/308,866 entitled Multiple Function Applicator for Adhesives and filed on Aug. 1, 2001, the entire content of which is hereby incorporated by reference.

TECHNICAL FIELD

The present invention relates to adhesive applicators in general and to applicators for medical adhesives in particular.

BACKGROUND OF THE INVENTION

Many different applicators for glues and adhesives have been developed. Unfortunately, some applicators are specifically designed to supply very small amounts of adhesive with pinpoint accuracy; whereas, other applicators have been specifically designed to supply large amounts of adhesives over wide surface areas.

To date, applicators have not been developed with sufficient versatility to apply adhesives either in very small amounts with pinpoint accuracy, or over wide surface areas. Such applicators are specifically desirable in medical applications where the same adhesive compound may be used to close an open cut or wound, to seal the cut or wound, and then to dress the cut or wound.

SUMMARY OF THE INVENTION

The present invention provides a versatile applicator which is ideally suited for controlled application of adhesives, especially medical adhesives. As such, the present invention is particularly useful in closing and sealing wounds and protecting tissue.

In a preferred aspect, the present invention comprises an adhesive applicator, including a body having an internal reservoir and an opening between the internal reservoir and the exterior of the body; a sponge disposed over the opening; a slotted tip nozzle disposed over the sponge; and a small orifice tip nozzle disposed over the slotted tip nozzle. In various aspects, the slotted tip nozzle is releasably attached to the body of the applicator, and the small orifice tip nozzle is releasably attached either to the slotted tip nozzle, or directly to the body of the applicator. In accordance with the present invention, the small orifice tip nozzle may be removed first, followed by the removal of the slotted tip nozzle.

In a preferred method of use, a cut or open wound can be sequentially closed, sealed and then dressed, as follows. First, the wound is closed by applying small drops of adhesive to the wound, the small drops being applied by forcing the adhesive from the internal reservoir through the sponge, through the slotted tip nozzle and then through the small orifice tip nozzle and into the wound. Then, after the wound is closed, the small orifice tip nozzle may be removed. Then, the wound may be sealed by applying a line of adhesive with the slotted tip nozzle. Then, after the wound has been sealed, the slotted tip nozzle may be removed. Lastly, the wound may be dressed by applying further adhesive and/or spreading the adhesive around the area of the wound with the sponge.

Thus, advantages of the present invention include its ability to provide a versatile system which can be used to apply adhesives either as single small drops, in a thin line, in a wide line, or as a wide surface coating.

In preferred aspects, the body is deformable such that squeezing on the body forces contents of the internal reservoir out through the opening in the applicator body.

Also, in preferred aspects, the adhesive applied is a medical adhesive. Most preferably, the medical adhesive is a cyanoacrylate compound.

DETAILED DESCRIPTION OF THE DRAWINGS

Figure 1:
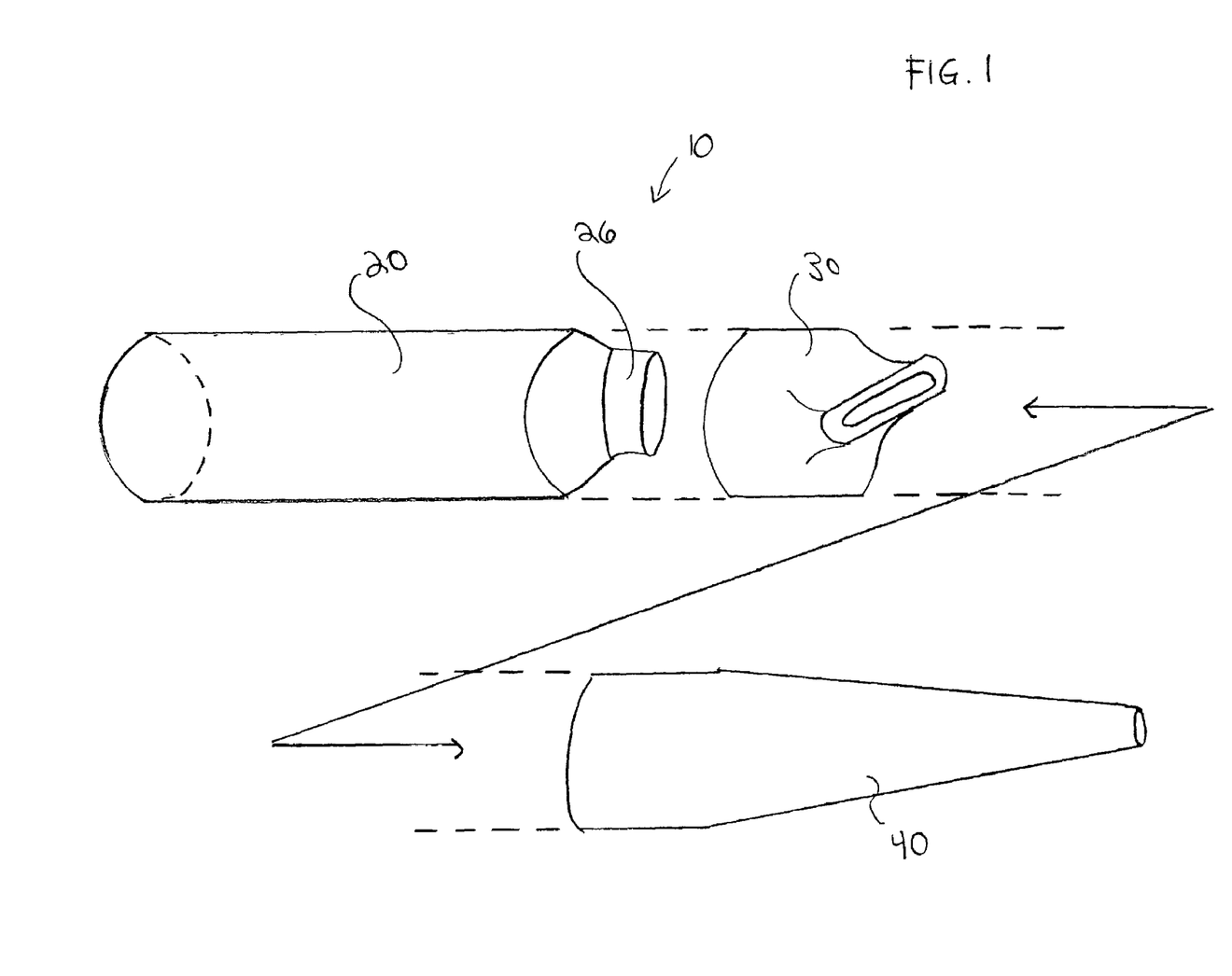
FIG. 1 is an exploded perspective view of the applicator of the present invention.
Figure 2:
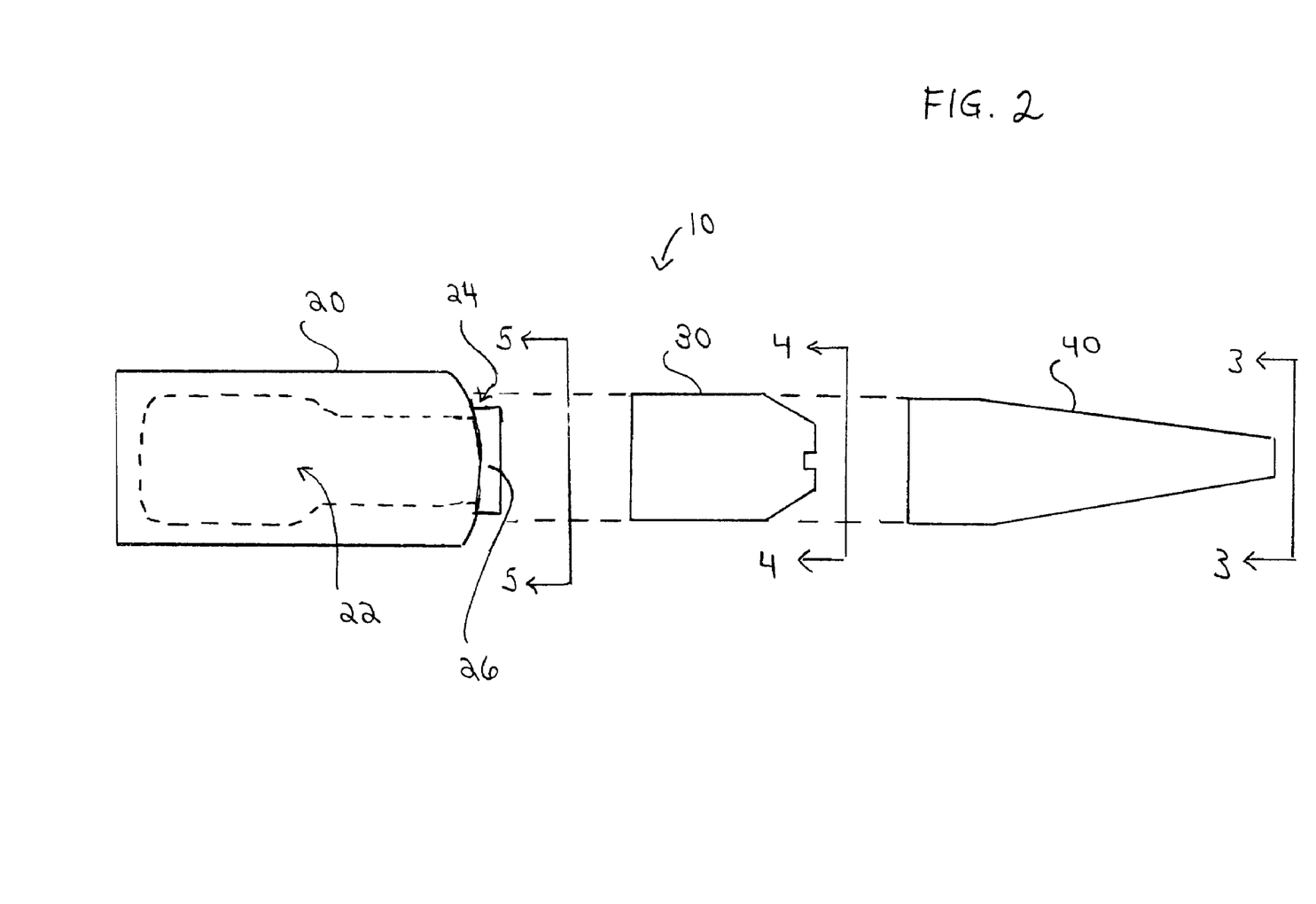
FIG. 2 is a side elevation view corresponding to FIG. 1.
Figure 3:
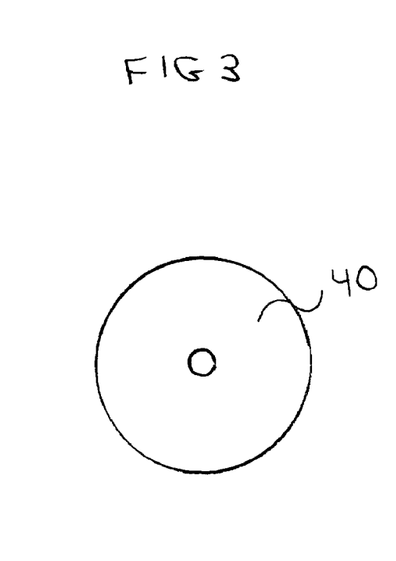
FIG. 3 is a front elevation view taken along line 3—3 in FIG. 2, showing the small orifice tip (which is positioned over the slotted tip).
Figure 4:
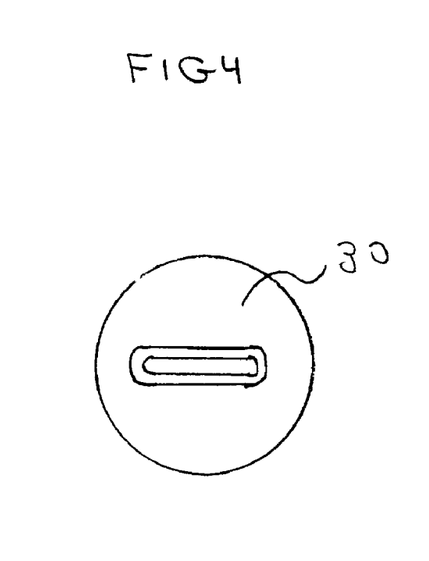
FIG. 4 is a front elevation view taken along line 3—3 in FIG. 2, showing the slotted tip (which is positioned over the sponge).
Figure 5:
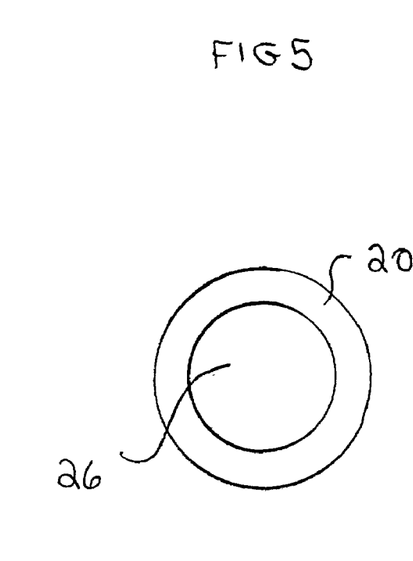
FIG. 5 is a front elevation view taken along line 5—5 in FIG. 2, showing the sponge (which is disposed over an opening on the body of the device).

FIGS. 1 and 2 are exploded perspective views of the applicator of the present invention showing an applicator 10 which includes a body 20, a slotted tip nozzle 30 and a small orifice tip nozzle 40. Body 20 has an internal reservoir 22 which is shown in dotted lines. As will be explained, slotted tip nozzle 30 is preferably removably attached to body 20 and small orifice tip nozzle 40 is preferably removably attached to slotted tip nozzle 30 (or directly to body 20).

Preferably, body 20 is deformable, such that the contents of internal reservoir 22 can be expelled through opening 24 by simply squeezing on body 20. Opening 24 is preferably fitted with a sponge 26 received therein. It is to be understood that the term "sponge" is not limiting, and may include any suitable fiber bunch or woven pad. As will be explained, sponge 26 can be used for spreading the contents of internal reservoir 22 over a wide surface area when slotted tip nozzle 30 and small orifice tip nozzle 40 have been removed. As such, sponge 26 functions as a porous "wicking pad" which assists both in drawing the adhesive out of internal reservoir 22, and in spreading the adhesive.

Slotted tip nozzle 30 is connected to body 20 such that it covers sponge 26. Preferably, slotted tip nozzle 30 is dimensioned such that it can simply be pressure fit into connection with body 20. By squeezing body 20, the adhesive is forced out of internal reservoir 22, through sponge 26 and then through slotted tip 30. Thus, when small orifice nozzle tip nozzle 40 is removed, the adhesive stored in internal reservoir 22 can be dispensed through slotted tip nozzle 30 in a line on a tissue surface. Moreover, by rotating applicator 10 about its central longitudinal axis when dispensing adhesives through slotted tip nozzle 30, the operator is able to control the width of the line of adhesive which is spread over the tissue surface (similar to the way a calligraphy pen is used). In one preferred aspect of the invention, the nozzle end opening of slotted tip nozzle 30 has a width of between 1/3 and 2/3 of the width of sponge 26.

Small orifice tip nozzle 40 is connected either to slotted tip nozzle 30 or to body 20 such that it covers slotted tip 30. Preferably, small orifice tip nozzle 40 is dimensioned such that it can simply be pressure fit into connection with slotted tip nozzle 30 or with body 20. By squeezing the contents out of internal reservoir 22, through sponge 26, through slotted tip nozzle 30, and then out through small orifice tip nozzle 40, the adhesive stored in internal reservoir 22 can be dispensed as small precise drops on a tissue surface.

In an optional preferred aspect of the present invention, internal reservoir 22 is filled with a medical cyanoacrylate adhesive formulation. In one embodiment, the cyanoacrylate adhesive formulation is stored in a crushable glass ampoule disposed within internal reservoir 22.

Figure 6:
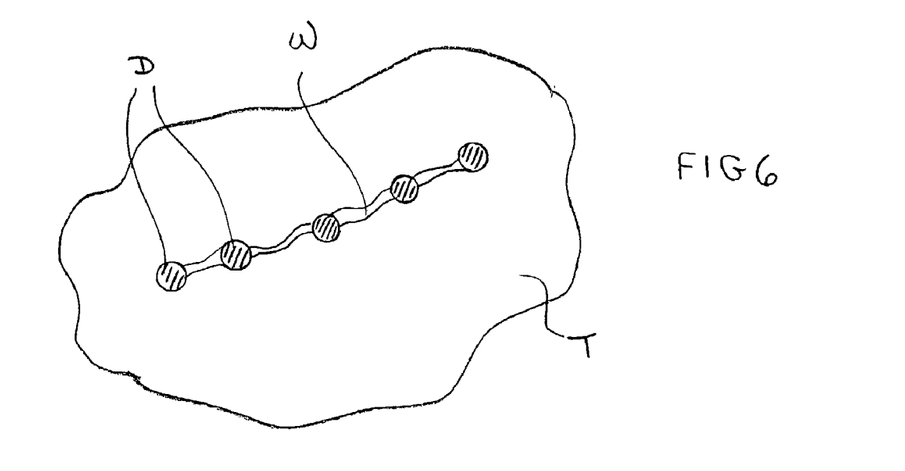
FIG. 6 shows a tissue surface with an open wound, with small adhesive drops disposed along the length of the wound to close the wound.

In a preferred method of operating the present invention, applicator 10 is provided with slotted tip nozzle 30 and small orifice tip nozzle 40 attached thereto. A patient having a tissue surface T with open wound W is treated, as follows. First, as shown in FIG. 6, wound W is closed by dispensing a plurality of small drops D of adhesive onto the skin surface to hold the skin closed along the length of the wound. At this time, both slotted tip nozzle 30 and small orifice tip nozzle 40 are attached to body 20, with the small drops D of adhesive being dispensed from the small orifice at the distal end of the small orifice tip nozzle 40.

Figure 7:
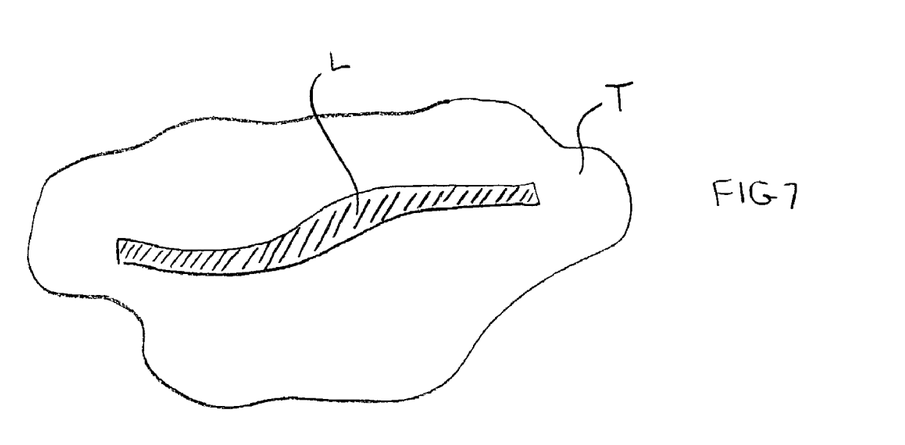
FIG. 7 shows a tissue surface with a line of adhesive spread so as to cover and thereby seal the wound.

Thereafter, small orifice tip nozzle 40 is removed. As shown in FIG. 7, a line L of adhesive is then spread over and a little beyond the length of the wound using slotted tip nozzle 30. This procedure seals the wound. By rotating the applicator, slotted tip nozzle 30 can be rotated, thus controlling the width of the line L of adhesive applied (similar to the way a calligraphy pen is used). At this time, the clinician may squeeze on body 20 to force more adhesive onto the tissue surface.

Figure 8:
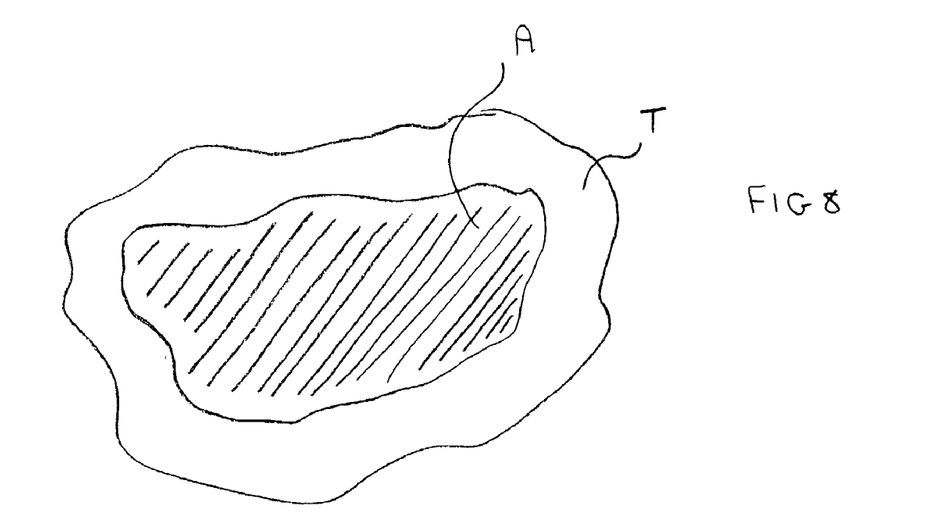
FIG. 8 shows a tissue surface with adhesive spread widely thereover, thereby dressing the wound therebelow.

Thereafter, slotted tip nozzle 30 is removed. As shown in FIG. 8, a wide area A of adhesive is then spread over the region adjacent to the wound using sponge 26. Thus, the tissue near the cut or wound is effectively covered. This procedure dresses the wound.

The present invention is not limited to those embodiments and examples presented herein. Thus, the following two examples of use of the present invention are presented as examplary uses and are not meant to be limiting.

EXAMPLE 1

A teenager presents at the emergency room with multiple cuts and abrasions after falling off his bicycle. One of the cuts is deep and six centimeters long and the emergency room physician closes it with 3-O mono-filament nylon suture. The physician then uses the present pre-assembled sterile medical cyanoacrylate adhesive applicator that is composed of: 0.7 grams of butyl cyanoacrylate enclosed in a crushable glass ampoule that is itself enclosed in a flexible butyrate tube (body 20) sealed at one end and closed with a wicking pad (sponge 26) at the other. Onto this flexible tube (body 20), over the wicking pad (sponge 26), the physician attaches a short slotted nozzle (slotted tip nozzle 30), and over the slotted nozzle he attaches a long pointed nozzle (small orifice nozzle 40). The physician then crushes the ampoule by squeezing on the butyrate tube thereby releasing the adhesive. The physician then squeezes the flexible tube until the adhesive reaches the end of the pointed nozzle (small orifice nozzle 40). The physician uses the applicator (device 10) to deposit small pinpoint drops of adhesive at 0.5 cm intervals along two shallow cuts of about three centimeters long each. In this way "spot welds" are applied to the cuts at intervals along the cut while the physician holds them closed. When the physician has adequately closed the two small cuts, the pointed nozzle (40) is removed to expose the slotted nozzle (30). The physician then wipes the nozzle (30) clean of free adhesive with a gauze pad and proceeds to cover the two small cuts with a 3 mm wide band of adhesive to seal them. The physician then uses the same nozzle (30) to seal the larger incision he closed with sutures earlier by applying adhesive to the areas of the cut between the sutures. The slotted nozzle (30) is then removed and the pad (26) is used to apply an adhesive protective coating over several of the abrasions that are not deep enough to require suturing.

EXAMPLE 2

A young female presents in the emergency room with a long shallow knife wound. After cleansing the wound, the clinician assembles a sterile medical cyanoacrylate adhesive applicator that contains 1 gram of anti-microbial butyl cyanoacrylate formulation containing a soluble poloxamer based iodophor. The cyanoacrylate adhesive formulation is enclosed in a crushable glass ampoule that is itself enclosed in a flexible butyrate tube (body 20) sealed at one end and closed with a wicking pad (sponge 26) at the other. Onto this flexible tube, over the wicking pad, she attaches a short slotted nozzle (30), and over the slotted nozzle she attaches a long pointed nozzle (40). The clinician then crushes the ampoule by squeezing on the butyrate tube thereby releasing the anti-microbial adhesive solution. The clinician then closes the wound (FIG. 6) by using the pointed applicator tip to deposit small pinpoint "spot welds" of anti-mirobial adhesive at 0.5 cm intervals along the cut while she holds the relevant portion closed. She then removes the pointed nozzle (40) to expose the slotted nozzle (30), wipes this nozzle (30) clean of free adhesive with a gauze pad and proceeds to cover the cut with a 3 mm wide band of anti-microbial adhesive to seal it (FIG. 7). The clinician then removes the slotted nozzle (30) and uses the pad (26) to apply an anti-microbial protective dressing over and around the cut (FIG. 8).

Cyanoacrylate Adhesive Compositions

The adhesives which are applied by the applicator of the present invention may preferably comprise a wide variety of cyanoacrylate adhesive formulations. It is to be understood, however, that the present invention is not so limited. Instead, any suitable medical (or non-medical) adhesive can be used.

In accordance with an optional preferred aspect of the present invention, a cyanoacrylate adhesive formulation is used. Preferably, the cyanoacrylate composition used comprises a cyanoacrylate prepolymer composition that can be applied as a liquid to the skin surface. Optionally, the cyanoacrylate prepolymer can include therapeutic agents such as analgesics, anti-inflammatory agents, antimicrobial agents, and the like.

Most preferably, the polymerizable cyanoacrylate ester comprises an ester which, in monomeric form, is represented by formula I:

where R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and more preferably alkyl of from 2 to 8 carbon atoms. Even more preferably, R is butyl, pentyl or octyl and most preferably, R is n-butyl.

It is to be understood that a the term "polymerizable cyanoacrylate esters" refers to polymerizable formulations comprising cyanoacrylate monomers or polymerizable oligomers which, in their monomeric form, are preferably compounds represented by formula I as described above.

More preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl. Mixtures of such compounds can also be employed as disclosed by Berger, et al., U.S. Pat. No. 5,998,472 which is incorporated herein by reference in its entirety.

A preferred cyanoacrylate ester for use in the invention is n-butyl-2-cyanoacrylate.

The polymerizable cyanoacrylate esters described herein rapidly polymerize in the presence of water vapor or tissue protein, and the n-butyl-cyanoacrylate bonds to mammalian skin tissue without causing histotoxicity or cytotoxicity.

Such polymerizable cyanoacrylate esters are sometimes referred to herein as prepolymers and compositions comprising such esters are sometimes referred to herein as prepolymer compositions.

Polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

Optionally, the cyanoacrylate composition applied by the present applicator can include a "biocompatible plasticizer". As used herein, the term "biocompatible plasticizer" refers to any material which is soluble or dispersible in the cyanoacrylate composition, which increases the flexibility of the resulting polymeric film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate, acetyl tri-hexyl citrate butyl benzyl phthalate, dibutyl phthalate, dioctylphthalate, n-butyryl tri-n-hexyl citrate, diethylene glycol dibenzoate and the like. The particular biocompatible plasticizer employed is not critical and preferred plasticizers include dioctylphthalate and $C_2$–$C_4$-acyl tri-n-hexyl citrates.

Optionally as well, the cyanoacrylate composition applied by the present applicator can include an "antimicrobial agent". As used herein, the term "antimicrobial agent" refers to agents which destroy microbes (i.e., bacteria, fungi, yeasts, prions5 and viruses) thereby preventing their development and their pathogenic action.

Preferred cyanoacrylate compositions useful in the practice of this invention are also disclosed by Greff, et al., U.S. Pat. No. 5,480,935, which application is incorporated herein by reference in its entirety. In a particularly preferred embodiment, the cyanoacrylate adhesive composition further comprises an antimicrobially effective amount of a compatible antimicrobial agent. Such compositions preferably comprise from about 0.1 to about 40 and preferably 1 to 30, or more preferably 5 to 20 weight percent of the compatible antimicrobial agent either as a solution or as a suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin. Suitable such compositions are disclosed in U.S. Pat. No. 6,224,799 which discloses compositions of cyanoacrylate/povidone-iodine complexes and U.S. patent application Ser. No. 09/215,078 which discloses compositions of cyanoacrylate esters/iodine complexes of polyoxyalkylene polymers. Both applications are incorporated herein by reference in their entirety.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidone polymer which, when complexed with iodine, is also referred to under the common name of povidone-iodine available from BASF, Mt. Olive, N.J., USA. When povidone-iodine is employed in the cyanoacrylate composition, it is preferably from about 5 to about 40 weight percent and more preferably from about 10 to 25 weight percent is added to the cyanoacrylate composition based on the total weight of the composition.

Other suitable antimicrobial agents include complexes of iodine molecules with copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like.

The use of a compatible antimicrobial agent in the composition permits the agent to be released from the polymeric film thereby reducing microbial growth under the film.

Other medicaments suitable for use in conjunction with the cyanoacrylate composition include corticoid steroids such as described by Greff, et al. in U.S. Pat. No. 5,962,010 which is incorporated herein by reference in its entirety and analgesic compounds such as lidocaine. The former reduces inflammation at the site of the application whereas the latter reduces pain. Combinations of a steroid with an analgesic are also covered.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A method of closing, sealing and dressing a wound with an adhesive applicator comprising a body with an internal reservoir, adhesive disposed in the internal reservoir and an opening between the internal reservoir and the exterior of the body; a sponge disposed over the opening; a slotted tip nozzle disposed over the sponge; and a small orifice tip nozzle disposed over the slotted tip nozzle; comprising:

closing the wound by applying small drops of adhesive to the wound, the small drops being applied by forcing the adhesive from the internal reservoir through the sponge, through the slotted tip nozzle and then through the small orifice tip nozzle;

removing the small orifice tip nozzle;

sealing the wound by applying a line of adhesive to the wound with the slotted tip nozzle;

removing the slotted tip nozzle; and dressing the wound by applying further adhesive to the wound with the sponge.

2. The method of claim 1, wherein forcing the adhesive from the internal reservoir through the sponge, through the slotted tip nozzle and then through the small orifice tip nozzle by squeezing on the body of the applicator.

3. The method of claim 1, further comprising:

adjusting the width of the line of adhesive applied by the slotted tip nozzle by rotating the applicator, thereby rotating the slotted tip nozzle.

4. The method of claim 1, wherein the adhesive is a medical adhesive.

5. The method of claim 4, wherein the medical adhesive is a cyanoacrylate ester, in monomeric form, represented by formula I:

where R is selected from the group consisting of:
alkyl of 1 to 10 carbon atoms,
alkenyl of 2 to 10 carbon atoms,
cycloalkyl groups of from 5 to 8 carbon atoms, phenyl,
2-ethoxyethyl,
3-methoxybutyl,
and a substituent of the formula:

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

6. An applicator for closing, sealing and dressing a wound with liquid adhesive comprising a body with an internal reservoir capable of containing said liquid adhesive, a liquid adhesive-communicating opening between the internal reservoir and the exterior of the body; a liquid adhesive-permeable sponge disposed over the opening; a slotted tip nozzle removably disposed over the sponge; and a small orifice tip nozzle removably disposed over the slotted tip nozzle; the applicator permitting;

closure of the wound by applying small drops of the liquid adhesive to the wound to produce a closed wound, the small drops provided by passing a first portion of liquid adhesive from the internal reservoir, through the opening, through the sponge, through the slotted tip nozzle and finally through the small orifice tip nozzle to the wound:

removal of the small orifice tip nozzle to form an applicator without a small orifice tip nozzle; the applicator without a small orifice tip nozzle permitting;

sealing of the closed wound by applying a line of the liquid adhesive to the closed wound to produce a sealed wound, the line provided by passing a second portion of liquid adhesive from the internal reservoir, through the opening, through the sponge, and finally through the slotted tip nozzle to the closed wound:

and removal of the slotted tip nozzle to form an applicator without a small orifice tip nozzle or a slotted tip nozzle, the applicator without a small orifice tip nozzle or a slotted tip nozzle permitting;

dressing of the sealed wound by applying a layer of the liquid adhesive to the closed wound to produce a dressed wound; the layer provided by passing a third portion of liquid adhesive from the internal reservoir, through the opening, and finally through the sponge to the sealed wound.

7. The adhesive applicator of claim 6, wherein the small orifice tip nozzle is releasably attached to the slotted tip nozzle.

8. The adhesive applicator of claim 6, wherein the small orifice tip nozzle is releasably attached to the body.

9. The adhesive applicator of claim 6, wherein the body is such that squeezing on the body forces contents of the internal reservoir out through the opening in the applicator body.

10. The adhesive applicator of claim 6, further comprising: a medical liquid adhesive in the internal reservoir.

11. The adhesive applicator of claim 10, wherein the medical adhesive is a cyanoacrylate ester, in monomeric form, represented formula I:

I where R is selected from the group consisting of:
   alkyl of 1 to 10 carbon atoms,
   alkenyl of 2 to 10 carbon atoms,
   cycloalkyl groups of from 5 to 8 carbon atoms,
   phenyl,
   2-ethoxyethyl,
   3-methoxybutyl,
   and a substituent of the formula:

wherein each R' is independently selected from the group consisting of:
   hydrogen and methyl, and
   R" is selected from the group consisting of:
   alkyl of from 1 to 6 carbon atoms,
   alkenyl of from 2 to 6 carbon atoms,
   alkynyl of from 2 to 6 carbon atoms,
   cycloalkyl of from 3 to 8 carbon atoms,
   aralkyl selected from the group consisting of benzyl, methylbenzyl and phenylethyl,
   phenyl, and
   phenyl substituted with 1 to 3 substituents selected from the group consisting of hydroxy, chloro, bromo, nitro, of alkyl 1 to 4 carbon atoms, and alkoxy of from 1 to 4 carbon atoms.

12. The adhesive applicator of claim 6, wherein the nozzle of the slotted tip nozzle has a width of between ⅓ and ⅔ of the width of the sponge.

* * * * *

UNITED STATES PATENT AND TRADEMARK OFFICE
CERTIFICATE OF CORRECTION

PATENT NO. : 7,094,250 B2
APPLICATION NO. : 10/209317
DATED : August 22, 2006
INVENTOR(S) : Richard J. Stenton It is certified that error appears in the above-identified patent and that said Letters Patent is hereby corrected as shown below:

Claim 5, at column 8, line 15, replace:

"  I "

With the following:

Signed and Sealed this

Second Day of January, 2007

JON W. DUDAS
*Director of the United States Patent and Trademark Office*